United States Patent [19]

Bambury et al.

[11] 3,956,287

[45] May 11, 1976

[54] 7-[(2-OXO-1-PYRIDINYL)ACYLAMINO]-CEPHALOSPORIN DERIVATIVES

[75] Inventors: Ronald E. Bambury; Michael L. Edwards, both of Cincinnati; Laird F. Miller, Loveland, all of Ohio

[73] Assignee: Richardson-Merrell Inc., Wilton, Conn.

[22] Filed: Nov. 7, 1973

[21] Appl. No.: 413,566

[52] U.S. Cl. .......................... 260/243 C; 424/246; 424/271
[51] Int. Cl.² .............. C07D 501/20; C07D 499/44
[58] Field of Search .......................... 260/243 C

[56] References Cited
UNITED STATES PATENTS

| | | | |
|---|---|---|---|
| 3,218,318 | 11/1965 | Flynn | 260/243 C |
| 3,459,746 | 8/1969 | Flynn | 260/243 C |
| 3,553,203 | 1/1971 | Schwarz | 260/243 C |
| 3,757,013 | 9/1973 | Bickel et al. | 260/243 C |
| 3,855,213 | 12/1974 | Dunn et al. | 260/243 C |
| 3,867,380 | 2/1975 | Dunn et al. | 260/243 C |

*Primary Examiner*—Nicholas S. Rizzo
*Attorney, Agent, or Firm*—William J. Stein; Eugene O. Retter; George W. Rauchfuss, Jr.

[57] ABSTRACT

Novel [substituted(2-oxo-1-pyridinyl)acetylamino] penicillin and cephalosporin derivatives are prepared which are useful antibacterial agents.

5 Claims, No Drawings

3,956,287

7-[(2-OXO-1-PYRIDINYL)ACYLAMINO]CEPHALOSPORIN DERIVATIVES

FIELD OF THE INVENTION

This invention relates to novel derivatives of [substituted(2-oxo-1-pyridinyl)acetylamino] penicillins and cephalosporins, to their methods of preparation, and to their usefulness as antibacterial agents.

BACKGROUND OF THE INVENTION

This invention relates to new synthetic compounds of the penicillin and cephalosporin classes which are useful as antibacterial agents. These compounds possess a high degree of activity against a large number of microorganisms, particularly those penicillinase-producing microorganisms. As antibacterial agents the compounds of this invention are therapeutically effective in the treatment of infectious diseases due to gram-positive and gram-negative bacteria in poultry and animals, including man. In addition, the compounds of this invention are useful as animal feed supplements and as the active ingredient in germicidal preparations employed as surface disinfectants.

PRIOR ART

The cleavage of penicillins to 6-aminopenicillanic acid in 1959 and the chemical cleavage of cephalosporin to give the corresponding 7-aminocephalosporanic acid made possible the synthesis of new synthetic penicillins and cephalosporins not previously available via fermentation procedures. Acylation of the amino group has produced derivatives containing a heterocyclic ring in the 6-position side chain, as in the case of the penicillin series, or in the corresponding 7-position side chain, as in the case of the cephalosporin series. Such heterocycles include the thiophene ring, as for example, U.S. Pat. Nos. 3,218,318, 3,449,338 and 3,498,979 (cephaloridine and cephalothin); pyridine, U.S. Pat. No. 3,422,100 (cephapirin); picoline, U.S. Pat. No. 3,553,203; hydantoin, U.S. Pat. No. 3,227,712; and various other nitrogen containing heterocycles including pyrrolidine and nicotinic acid, U.S. Pat. No. 3,308,120.

In each instance the heterocyclic moiety is attached to a side chain, generally that of an acetyl radical, via one of the ring carbon atoms. The present invention is concerned with 2-oxo-1-pyridinyl derivatives which are linked directly to the acetyl radical through the hetero atom. Examples known to the inventors containing this type of linkage, and in this regard represent the closest prior art, are the tetrazole ring in U.S. Pat. No. 3,516,997 (cefazolin) and certain quinazolinyl derivatives of penicillanic acid, U.S. Pat. No. 3,652,547.

SUMMARY OF THE INVENTION

This invention relates to novel 2-oxo-1-pyridinyl penicillin and cephalosporin derivatives. More particularly, this invention relates to [substituted(2-oxo-1-pyridinyl)acetylamino] penicillin and cephalosporin derivatives which are useful as antibacterial agents and which may be represented by the general formula:

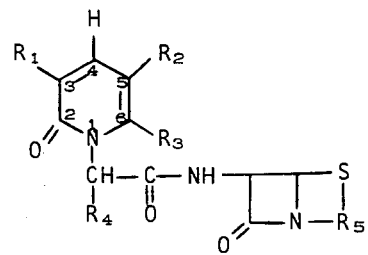

(I)

in which either $R_1$ or $R_2$ is selected from the group consisting of hydrogen, halogen, hydroxyl, lower alkyl, trifluoromethyl, nitro, amino, cyano, carboxy, carbomethoxy and carbethoxy;

$R_3$ is selected from the group consisting of hydrogen, halogen, hydroxyl, lower alkyl, trifluoromethyl, nitro, amino, cyano, carboxy, carbomethoxy, carbethoxy, and which when taken in combination with $R_2$ forms the cyclic radical $-CH_2CH_2CH_2CH_2-$ and $-CH=CH-CH=CH-$;

$R_4$ is selected from the group consisting of hydrogen, methyl, carboxy, carbomethoxy and carbethoxy;

$R_5$ is selected from the group consisting of the radicals

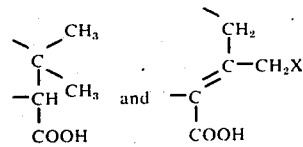

wherein X is hydrogen, hydroxy, acetoxy, N-pyridinium, 5-methyl-1,3,4-thiadiazol-2-ylthio and 1-methyl-1,2,3,4-tetrazol-5-ylthio; and the pharmaceutically acceptable salts thereof.

The compounds of the present invention are prepared by the condensation of a 6-aminopenicillanic acid or a 7-aminocephalosporanic acid with a (substituted)2-oxo-1-pyridinylacetic acid as illustrated in the following reaction scheme.

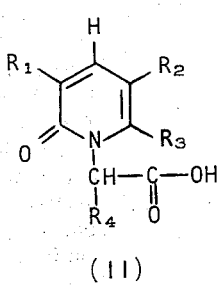

(II)

+

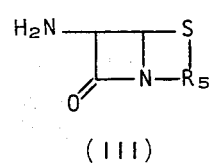

(III)

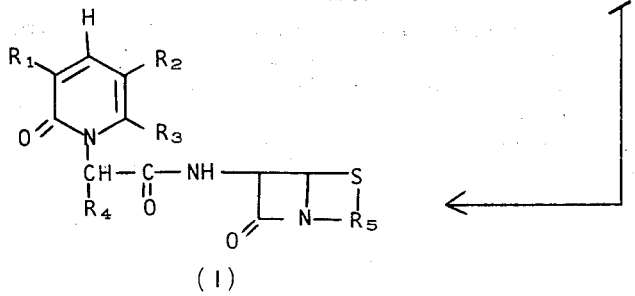

(I)

DETAILED DESCRIPTION OF THE INVENTION

All of the compounds of the present invention contain a 2-oxo-1-pyridinyl radical or a 2-pyridone moiety at the terminal position of the acetylamino side chain, as indicated in general Formula (I) above. In the case of the penicillin series, the acetylamino side chain is enumerated as the 6-position, whereas in the cephalosporin series of compounds the 7-position is enumerated. The numbering system for these two series of compounds is illustrated for the intermediates 6-aminopenicillanic acid (IV) and 7-aminocephalosporanic acid (V) below:

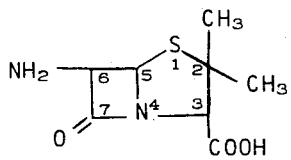

(IV)

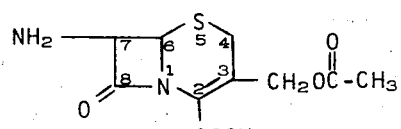

(V)

The 2-pyridone moiety attached to the acetylamino side chain may be substituted or unsubstituted. In general these substituents are all mono-substituents and are present in either the 3-,5- or 6-positions of the pyridine nucleus. These substituents include the following radicals: halogen, hydroxyl, lower alkyl, trifluoromethyl, nitro, amino, cyano, carboxyl and the methyl and ethyl esters of the carboxyl radical. The term halogen includes the fluoro, chloro, bromo and iodo radicals. The term lower alkyl as used herein includes both straight and branched chain aliphatic hydrocarbon radicals having from 1 to 4 carbon atoms. Specifically included are such members as methyl, ethyl, propyl, isopropyl, butyl, isobutyl, and the t-butyl radicals.

In addition to the various mono-substituents described above, the 2-pyridone moiety can be considered as di-substituted in two situations. Thus, the symbol $R_3$ when taken together with the adjacent $R_2$ can be viewed as forming an attached alicyclic or aromatic derivative at the 5,6-position of the pyridine ring. More properly, these derivatives can be termed as 2-[substituted(2-oxo-1-quinolinyl)] and 2-[substituted(2-oxo-1-tetrahydroquinolinyl)]acetylamino derivatives of penicillins and cephalosporins.

In addition to the mandatory substitution of the 2-methyl group of the acetylamino or acetamido portion of the molecule with 2-oxo-1-pyridinyl radical, the 2-methyl group may contain additional substitution in the form of a methyl radical or a carboxyl radical as represented by the symbol $R_4$. When $R_4$ is methyl, the compounds are more properly termed as propionyl derivatives of 6-aminopenicillanic acid or of 7-aminocephalosporanic acid. However, for the sake of uniformity in nomenclature, they are termed as 2-(substituted)acetylamino derivatives herein. Thus, for example, in the case of a cephalosporanic acid derivative in which $R_4$ is methyl and the 2-pyridone is unsubstituted, the compound is designated as 7-[2-(2-oxo-1-pyridyl)-2-methylacetylamino]cephalosporanic acid. In addition to the carboxyl radical at $R_4$ the methyl and ethyl esters or carbomethoxy and carbethoxy radicals are also contemplated to be within the scope of the present invention.

This invention is essentially concerned with the preparation and description of 2-(2-oxo-1-pyridinyl)acetylamino derivatives of β-lactam antibiotics. Thus, these derivatives are prepared by condensation with the readily available 6-amino penicillanic acid or any of the available 7-aminocephalosporin intermediates. Thus, where $R_5$ is the radical

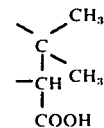

derivatives of the penicillin series are delineated, whereas when $R_5$ is the radical

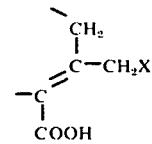

derivatives of the cephalosporin series are described.

Variations within the cephalosporin in series are further indicated by the symbol X. Thus, where X is hydrogen the desacetoxycephalosporanic acids are delineated; and where the symbol X is hydroxyl, the desacetylcephalosporanic acids are indicated. Where the symbol X represents an acetoxy radical the β-lactam nucleus is that of cephalosporanic acid. Additional substituents at the 3-position of decephalosporanic acid which are included within the purview of the present invention and represented by the symbol X are the 3-pyridiniummethyl, the 3-(5-methyl-1,3,4-thiadiazol- 2-ylthio)methyl and the 3-(1-methyl-1,2,3,4-tetrazol-5-ylthio)methyl radicals.

The pharmaceutically acceptable salts of the compounds of Formula (I) above include the non-toxic, carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and additional amines which have been used to form non-toxic salts with benzylpenicillin. These salts can be prepared using conventional means such as contacting and neutralizing a solution of the carboxylic acid in a polar solvent with a stoichiometric quantity of base.

Illustrative specific base compounds which are encompassed by Formula (I) above include: 6-[2-(2-oxo-1-pyridinyl)acetylamino]penicillanic acid, 6-[2-(6-hydroxy-2-oxo-1-pyridinyl)acetylamino]penicillanic acid, 6-[2-(3-ethyl-2-oxo-1-pyridinyl)-2-methylacetylamino]penicillanic acid, 6-[2-(5-trifluoromethyl-2-oxo-1-pyridinyl)-2-carboxyacetylamino]penicillanic acid, 6-[2-(3-nitro-2-oxo-1-pyridinyl)-2-(carbomethoxy)acetylamino]penicillanic acid, 6-[2-(6-cyano-2-oxo-1-pyridinyl)acetylamino]penicillanic acid, 6-[2-(5-carboxy-2-oxo-1-pyridinyl)-2-(carbethoxy)acetylamino]penicillanic acid, 7-[2-(2-oxo-1-pyridinyl)acetylamino]cephalosporanic acid, 7-[2-(5-propyl-2-oxo-1-pyridinyl)acetylamino]cephalosporanic acid, 7-[2-(5-hyroxy-2-oxo-1-pyridinyl)acetylamino]cephalosporanic acid, 7-[2-(6-carbomethoxy-2-oxo-1-pyridinyl)acetylamino]cephalosporanic acid, 7-[2-(2-oxo-1-quinolinyl)acetylamino]cephalosporanic acid, 7-[2-(3-cyano-2-oxo-1-pyridinyl)-2-methylacetylamino]cephalosporanic acid, 7-[2-(2-oxo-1-pyridinyl)acetylamino]desacetoxycephalosporanic acid, 7-[2-(3-amino-2-oxo-1-pyridinyl)-2-(carbomethoxy)acetylamino]desacetoxycephalosporanic acid, 7-[2-(5-nitro-2-oxo-1-pyridinyl)-2-(carboxy)acetylamino]desacetoxycephalosporanic acid, 7-[2-(3-carbethoxy-2-oxo-1-pyridinyl)acetylamino]-desacetoxycephalosporanic acid, 7-[2-(6-trifluoromethyl-2-oxo-1-pyridinyl)-2-methylacetylamino]desacetoxycephalosporanic acid, 7-[2-(2-oxo-1-pyridinyl)acetylamino]desacetylcephalosporanic acid, 7-[2-(3-butyl-2-oxo-1-pyridinyl)-2-(carboxy)acetylamino]desacetylcephalosporanic acid, 7-[2-(5-carboxy-2-oxo-1-pyridinyl)-2-methylacetylamino]desacetylcephalosporanic acid, 7-[2-(6-hydroxy-2-oxo-1-pyridinyl)-2-(carbomethoxy)acetylamino]desacetylcephalosporanic acid, 7-[2-(3-nitro-2-oxo-1-pyridinyl)acetylamino]desacetylcephalosporanic acid, 7-[2-(2-oxo-1-tetrahydroquinolinyl)acetylamino]desacetylcephalosporanic acid, 7-[2-(2-oxo-1-pyridinyl)acetylamino]-3-(pyridiniummethyl)decephalosporanic acid, 7-[2-(6-amino-2-oxo-1-pyridinyl)-2-(carbomethoxy)acetylamino]-3-(pyridiniummethyl)decephalosporanic acid, 7-[2-(5-methyl-2-oxo-1-pyridinyl)-2-(carboxy)acetylamino]-3-(pyridiniummethyl)decephalosporanic acid, 7-[2-(3-trifluoromethyl-2-oxo-1-pyridinyl)-2-(carbethoxy)acetylamino]-3-(pyridiniummethyl)decephalosporanic acid, 7-[2-(6-cyano-2-oxo-1-pyridinyl)acetylamino]-3-(pyridiniummethyl)-decephalosporanic acid, 7-[2-(2-oxo-1-quinolinyl)-2-methylacetylamino]-3-(pyridiniummethyl)decephalosporanic acid, 7-[2-(2-oxo-1-pyridinyl)acetylamino]-3-[(5-methyl-1,3,4-thiadiazol-2-ylthio)methyl]decephalosporanic acid, 7-[2-(6-cyano-2-oxo-1-pyridinyl)-2-(methyl)acetylamino]-3-[(5-methyl-1,3,4-thiadiazol-2-ylthio)methyl]decephalosporanic acid, 7-[2-(3-trifluoromethyl-2-oxo-1-pyridinyl)-2-(carbomethoxy)acetylamino]-3-[(5-methyl-1,3,4-thiadiazol-2-ylthio)methyl]decephalosporanic acid, 7-[2-(5-hydroxy-2-oxo-1-pyridinyl)acetylamino]-3-[(5-methyl-1,3,4-thiadiazol-2-ylthio)methyl]decephalosporanic acid, 7-[2-(2-oxo-1-quinolinyl)-2-(carbethoxy)acetylamino]-3-[(5-methyl-1,3,4-thiadiazol-2-ylthio)methyl]decephalosporanic acid, 7-[2-(2-oxo-1-pyridinyl)acetylamino]-3-](1-methyl-1,2,3,4-tetrazol-5-ylthio)methyl]decephalosporanic acid, 7-[2-(3-amino-2-oxo-1-pyridinyl)-2-(carboxy)acetylamino]-3-[(1-methyl-1,2,3,4-tetrazol-5-ylthio)methyl]decephalosporanic acid, 7-[2-(5-hydroxy-2-oxo-1-pyridinyl)-2-(carbomethoxy)acetylamino]-3-[(1-methyl-1,2,3,4-tetrazol-5-ylthio)methyl]decephalosporanic acid, 7-[2-(6-propyl-2-oxo-1-pyridinyl)-2-(carbethoxy)acetylamino]-3-[(1-methyl-1,2,3,4-tetrazol-5-ylthio)methyl]decephalosporanic acid, 7-[2-(3-carboxy-2-oxo-1-pyridinyl)-2-methylacetylamino]-3-[(1-methyl-1,2,3,4-tetrazol-5-ylthio)methyl]decephalosporanic acid, and 7-[2-(2-oxo-1-tetrahydroquinolinyl)-2-methylacetylamino]-3-[(1-methyl-1,2,3,4-tetrazol-5-ylthio)methyl]decephalosporanic acid.

The products of the present invention are prepared by reacting a β-lactam 6-aminopenicillanic acid or 7-aminocephalosporanic acid, or derivative thereof, having the formula

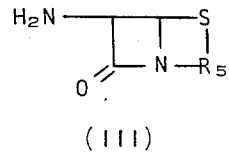

(III)

with a 2-oxo-1-pyridinyl carboxylic acid having the formula

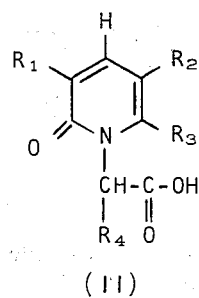

(II)

wherein the symbols $R_1$, $R_2$, $R_3$, $R_4$ and $R_5$ have the values previously assigned.

The β-lactam starting materials (III) are all known compounds. The compound, 6-aminopenicillanic acid, having the formula

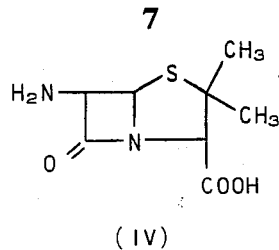

(IV)

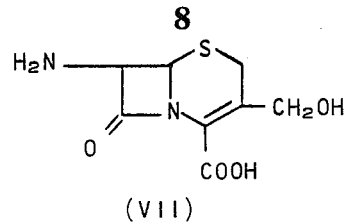

(VII)

can be prepared using biological methods and can also be prepared by the hydrolysis of various penicillins as described in U.S. Pat. No. 3,499,909.

Hydrolysis of the antibiotic cephalosporin in C results in the formation of 7-aminocephalosporanic acid, Loder, et al., Biochemical Journal 79, 408–416 (1961), having the formula

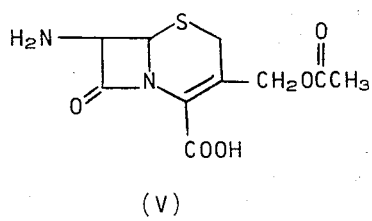

(V)

The compound 7-aminodesacetoxycephalosporanic acid having the formula

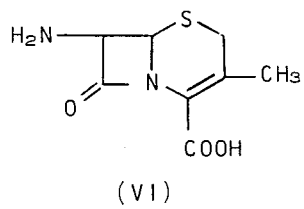

(VI)

is prepared by the catalytic reduction of cephalosporin C, followed by the hydrolytic removal of the 5-aminoadipoyl side chain as described in U.S. Pat. No. 3,129,224.

Treatment of cephalosporin C with an acetyl esterase prepared from orange peel, Jeffery et al., Biochem. J., 81, 591 (1961) results in the formation of 3-hydroxymethyl-7-aminodecephalosporanic acid or 7-aminodesacetylcephalosporanic acid having the formula Treatment of cephalosporin C with pyridine followed by an acid hydrolysis produces the compound, 7-amino-3-(pyridiniummethyl)decephalosporanic acid having the formula shown below. The preparation of this compound is known in the art and described, for example, in U.S. Pat. No. 3,117,126 and British Pat. Nos. 932,644, 957,570 and 959,054.

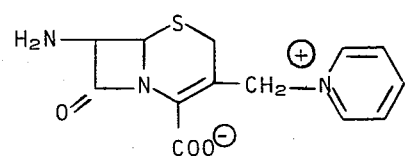

(VIII)

The 3-thiolated 7-aminocephalosporanic acids can be obtained by reacting 7-aminocephalosporanic acid with the appropriate thiol as described in U.S. Pat. No. 3,516,997. Thus when 5-methyl-1,3,4-thiadiazole-2-thiol is employed the compound 7-amino-3-[(5-methyl-1,3,4-thiadiazol-2-ylthio)methyl]decephalosporanic acid is obtained, which has the formula

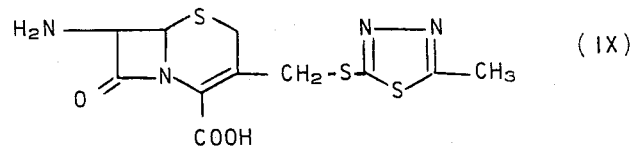

(IX)

When the compound 1-methyl-1,2,3,4-tetrazole-5-thiol is employed the compound 7-amino-3-[(1-methyl-1,2,3,4-tetrazol-5-ylthio)methyl]decephalosporanic acid is obtained having the formula

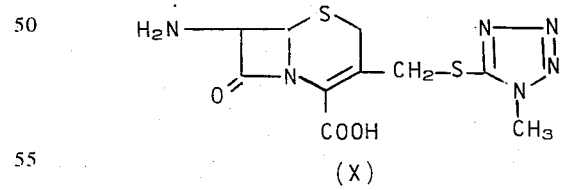

(X)

The 2-oxo-1-pyridinyl (substituted) acetic acids (II) used as starting materials are for the most part known compounds which are synthesized in one or two steps via the condensation of an alkali metal salt of a hydroxypyridine (XI) with ethylbromoacetate or a substituted ethylbromoacetate (XII). The potassium salt of hydroxypyridine is generally preferred to effect condensation, and the resulting ester hydrolyzed to the 2-oxo-1-pyridinyl (substituted) acetic acid (II) with an aqueous base as illustrated in the following reaction scheme:

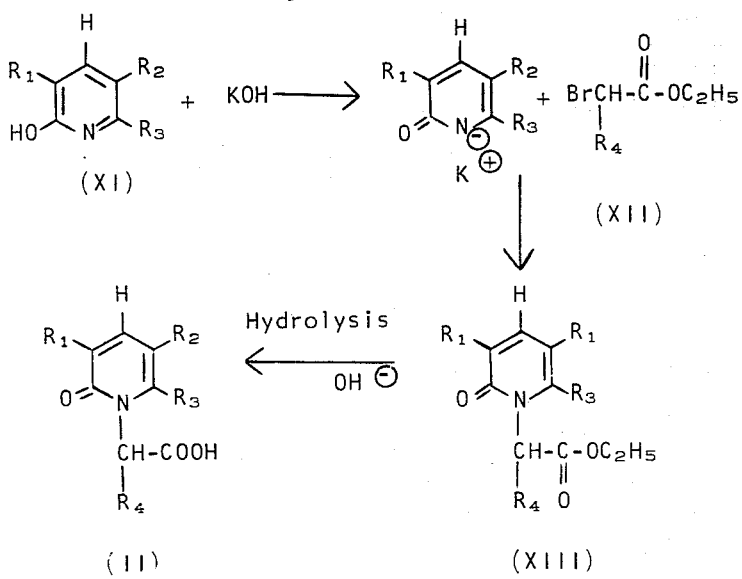

Alternatively, the 2-oxo-1-pyridinyl carboxylic acids (II) are directly prepared by reaction of a 2-pyridone (XI) with chloroacetic acid or a substituted chloroacetic acid (XIV) in the presence of a strong aqueous base as indicated in the following reaction scheme:

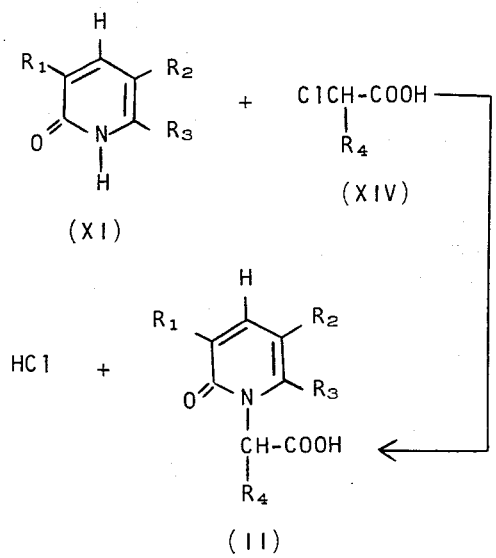

As an alternative to the direct coupling of 6-aminopenicillanic acid or of a 7-aminocephalosporanic acid (III) with a 2-oxo-1-pyridinyl carboxylic acid (II), the β-lactam acid may be coupled as its neutral salt (preferably as the sodium or triethylamine salt) or coupled as its β-lactam ester. Esters represented by Formula (III) are those in which the free carboxyl group of the β-lactam compound has been esterified. Since the ester group is to be removed followng the coupling reaction, preference is given to those ester groups which can be readily removed to regenerate the free carboxylic acid, as for example, by solvolysis, hydrogenolysis or via a nucleophilic exchange, without affecting or changing the remaining portion of the molecule. Esterification groups that are readily converted to the free carboxylic acid under mild conditions are the silylated and stannylated carboxyl groups. These groups are formed by treating compounds having a free carboxyl group with a suitable silylating agent, as for example, an alkyldisilazane such as hexamethyldisilazane. Suitable stannylating agents include, for example, a bis-(tri-lower alkyl-tin)oxide such as bis-(tri-n-butyl tin)oxide; a tri-lower alkyl tin-hydroxide such as triethyl tin hydroxide; a tri-lower alkoxy-tin compound such as triethoxy tin hydroxide; and a tri-loweralkyl-tin halide such as tri-n-butyl-tin chloride. The resulting silylated or stannylated carboxyl group can be regenerated to the desired free carboxylic acid by treatment with a neutral hydrogen-donating agent. Water or a lower alkanol, as for example, ethanol, is preferably used as the hydrogen-donating agent.

With regard to the 2-oxo-1-pyridinyl (substituted) acetic acids (II) which are used to couple with the 6-aminopenicillanic or 7-aminocephalosporanic acids, functional equivalents other than the free (substituted) acetic acid may also be employed. Examples of such reactive equivalents include the corresponding acid halides, acid azides, mixed acid anhydrides with alkylphosphoric acid or alkylcarbonic acid, acid amides with imidazole or a 4-substituted imidazole, acid cyanomethyl esters and acid p-nitrophenyl esters.

Preferably the coupling reaction is conducted in the presence of a condensing agent such as dicyclohexylcarbodiimide, N-cyclohexyl-N'-morpholinoethylcarbodiimide, pentamethyleneketone-N-cyclohexylimine, N-ethyl-o-phenylisoxazolium-3'-sulfonate, and phosphorous trichloride. Under such circumstances the reaction is believed to proceed through an active form of the carboxyl radical in the 2-oxo-1-pyridinyl (substituted) acetic acid or via the amino radical in the 6-aminopenicillanic acid or the 7-aminocephalosporanic acid.

The coupling reaction is generally conducted in the presence of a suitable solvent. Suitable solvents include acetone, dioxane, acetonitrile, chloroform, ethylene chloride, tetrahydrofuran or other inert, commonly used solvents. The reaction is further generally carried out in the presence of a base such as an alkali metal carbonate, trialkylamine or pyridine. Generally the reaction is conducted at room temperature or below.

Upon completion of the coupling reaction, generally after a period ranging from 30 minutes to 4 hours, the reaction product is isolated using conventional methods well known to those skilled in the art.

The novel compounds of the present invention are biologically active and have been found to possess good antibacterial activity. Thus, they are useful antimicrobial agents having a broad-spectrum antimicrobial activity in vitro against standard laboratory microorganisms which are used to screen for activity against pathogenic bacteria. The antibacterial spectrum of typical compounds of the present invention is determined in a standard manner by the agar-dilution streakplate technique commonly used in the testing of new antibiotics. The high in vitro antibacterial activity of the novel compounds of this invention not only makes them useful as pharmacological agents per se, but makes them useful as additives for animal feeds, as well as additives for materials which are subject to microbial deterioration, such as cutting oils and fuel oils. These compounds are also useful for their antibacterial effect in soaps, shampoos and in topical compositions for the treatment of wounds and burns.

The invention described herein is more particularly illustrated in conjunction with the following specific examples.

EXAMPLE 1

2-Pyridone-1-acetic acid

A mixture of 2-hydroxypyridine (47.5 grams, 0.5 mole), potassium hydroxide (28 grams, 0.5 mole) and ethanol (500 ml) is heated to reflux temperature and ethylbromoacetate (90 grams, 0.5 mole) is added dropwise. The reaction mixture is stirred at its reflux temperature for 2 hours and filtered. The filtrate is evaporated and an aqueous solution of 1 N sodium hydroxide (800 ml) is added to the residue. The aqueous mixture is stirred for 2 hours, chilled, acidified and filtered to give 2-pyridone-1-acetic acid. The solid is dissolved in a dilute aqueous sodium bicarbonate solution, and any solid is removed by filtration. The filtrate is acidified to give the desired 2-pyridone-1-acetic acid, m.p. 223°–5°C.

Substituting 6-methyl-2-hydroxypyridine, 5-chloro-2-hydroxypyridine, 5-nitro-2-hydroxypyridine and 3-methoxy-2-hydroxypyridine for the 2-hydroxypyridine above, there is obtained 6-methyl-2-pyridone-1-acetic acid, m.p. 218°C., 5-chloro-2-pyridone-1-acetic acid, m.p. 227°–229°C., 5-nitro-2-pyridone-1-acetic acid, m.p. 219°–223°C.; and 3-methoxy-2-pyridone-1-acetic acid, m.p. 185°–6°C.

EXAMPLE 2

6-Methyl-2-pyridone-1-acetic acid

A solution of 6-methyl-2-hydroxypyridine (21.8 grams, 0.2 mole) and chloroacetic acid (19 grams, 0.2 mole) in 50% aqueous potassium hydroxide (50 grams) is heated at its reflux temperature for 30 minutes, chilled, acidified and filtered. The solid so obtained is dissolved in an aqueous sodium bicarbonate solution and the solution is filtered. The filtrate is chilled, acidified and filtered to yield 6-methyl-2-pyridone-1-acetic acid, m.p. 218°C.

Substituting 5-chloro-2-hydroxypyridine, 2,6-dihydroxypyridine or 2-hydroxypyridine-3-carboxylic acid for the 6-methyl-2-hydroxypyridine in the above procedure, the following compounds are obtained, respectively: 5-chloro-2-pyridone-1-acetic acid, 6-hydroxy-2-pyridone-1-acetic acid and 3-carboxyl-2-pyridone-1-acetic acid.

EXAMPLE 3

7-[2-(2-Oxo-1-pyridinyl)acetylamino]cephalosporanic acid, sodium salt

The compound 2-pyridone-1-acetic acid (3.06 grams, 0.02 mole) is dissolved in dimethylformamide (50 ml) and the solution is chilled to 0°C. Carbonyldiimidazole (3.2 grams, 0.02 mole) is added and the mixture is stirred under nitrogen at 0°C. for 30 minutes and then warmed to room temperature. The reaction flask is evacuated for 30 minutes to remove the carbon dioxide and chilled to −20°C. In a separate flask, 7-aminocephalosporanic acid is silylated by heating a suspension of 7-aminocephalosporanic acid (5.4 grams, 0.02 mole) and hexamethyldisilazane (8 ml) in chloroform (50 ml) at reflux for 30 minutes. This solution is evaporated to dryness to remove the liberated ammonia. A solution of the residue in chloroform (50 ml) is chilled to −20°C. and added to the imidazolide. The reaction mixture is stirred at 0°C. for 1 hour, warmed to room temperature and stirred overnight.

The solution is treated with 2 ml of methanol and the precipitated 7-aminocephalosporanic acid is removed by filtration. A solution of sodium 2-ethylhexanoate in n-butanol (10 ml of a 2 N solution) is added, and the mixture is diluted with ether to an approximate volume of 1 liter in order to precipitate the product. After reprecipitation from methanol with ether, a yield of 1.3 grams of a white solid, m.p. 180°C. (dec.) is obtained. Iodine titration indicated a purity of 97.6%.

Following essentially the same procedure but substituting 5-chloro-2-pyridone-1-acetic acid, 2-quinolinone-1-acetic acid, methyl-2-pyridone-1-malonate, 6-hydroxy-2-pyridone-1-acetic acid, 3-butyl-2-pyridone-1-acetic acid, and 2-(2-pyridone-1-yl)propionic acid for 2-pyridone-1-acetic acid the sodium salts of the following compounds are obtained, respectively: 7-[2-(5-chloro-2-oxo-1-pyridinyl)acetylamino]cephalosporanic acid, 7-[2-(2-oxo-1-quinolinyl)acetylamino]cephalosporanic acid, 7-[2-(2-oxo-1-pyridinyl)-2-(carbomethoxy)acetylamino]cephalosporanic acid, 7-[2-(6-hydroxy-2-oxo-1-pyridinyl)acetylamino]cephalosporanic acid, 7-[2-(3-butyl-2-oxo-1-pyridnyl)acetylamino]cephalosporanic acid and 7-[2-(2-oxo-1-pyridinyl)-2-(methyl)acetylamino]cephalosporanic acid.

EXAMPLE 4

6-[2-(2-Oxo-1-pyridinyl)acetylamino]penicillanic acid, sodium salt

2-Pyridone-1-acetic acid (3.06 grams, 0.02 mole) and triethylamine (2grams, 0.02 mole) are dissolved in chloroform (50 ml). The solution is chilled to −15°C. and ethyl chloroformate (2.2 grams, 0.02 mole) is added. The mixture is stirred at −10° to −15°C. for 30 minutes and a chilled solution of silylated 6-aminopenicillanic acid (prepared as described in Example 3 using 4.4 grams, 0.02 mole of 6-aminopenicillanic acid and 8 ml of hexamethyldisilazane) in chloroform (50 ml) is added thereto. The mixture is stirred at −15°C. for 1 hour, warmed to room temperature, and diluted with an equal volume of dioxane. The precipitated triethylamine hydrochloride is removed by filtration and 2 ml of methanol is added to the filtrate. After 30 minutes at room temperature, the precipitated 6-aminopenicillanic acid is filtered.

Ten ml of a 2 N solution of sodium 2-ethylhexanoate in n-butanol is added to the filtrate and the product is precipitated with ether (700 ml). After 2 reprecipitations from methanol with ether, the product is vacuum dried to yield 3 grams of a white solid, m.p. 120°C. (dec.) Iodine titration indicates an 80.6% purity.

Following essentially the same procedure but substituting 5,6,7,8-tetrahydro-2-quinolone-1-acetic acid, methyl 2-pyridone-1-malonate, methyl 5-nitro-2-pyridone-1-malonate, 3-trifluoromethyl-2-pyridone-1-acetic acid and 3-cyano-2-pyridone-1-acetic acid for 2-pyridone-1-acetic acid the sodium salts of the following compounds are obtained respectively: 6-[2-(5,6,7,8-tetrahydro-2-oxo-1-quinolinyl)-2-acetylamino]penicillanic acid, 6-[2-(2-oxo-1-pyridinyl)-2-carbomethoxy)acetylamino]penicillanic acid, 6-[2-(5-nitro-2-oxo-1-pyridinyl)-2-(carbomethoxy)acetylamino]penicillanic acid, 6-[2-(3-trifluoromethyl-2-oxo-1-pyridinyl)acetylamino]penicillanic acid and 6-[2-(3-cyano-2-oxo-1-pyridinyl)acetylamino]penicillanic acid.

EXAMPLE 5

6-[2-(5-Chloro-2-oxo-1-pyridinyl)acetylamino]-penicillanic acid, sodium salt

A solution of 5-chloro-2-pyridone-1-acetic acid (1.7 grams, 0.0089 mole) in dimethylformamide (25 ml) is chilled to −5°C. and carbonyldiimidazole (1.5 grams, 0.009 mole) is added in one portion. The mixture is stirred at −5° to 0°C. under an atmosphere of nitrogen for 1 hour and evacuated for 15 minutes to remove the carbon dioxide evolved in the imidazolide formation.

At −10°C. a solution of 6-aminopenicillanic acid (1.9 grams, 0.009 mole) and triethylamine (2 grams, 0.02 mole) in chloroform (25 ml) is added. The reaction mixture is stirred at −10°C. for 1 hour, warmed to room temperature and 5 ml of a 2 N solution of sodium 2-ethylhexanoate in n-butanol is added. Precipitation of the product is completed by the addition of ether (500 ml). The solid is reprecipitated from methanol with ether and vacuum dried to give 2 grams of white solid, m.p. 203°–206°C.

EXAMPLE 6

6-[2-(3-Methoxy-2-oxo-1-pyridinyl)acetylamino]-penicillanic acid, sodium salt

A solution of 3-methoxy-2-pyridone-1-acetic acid (3.4 grams, 0.02 mole) in 50 ml of dimethylformamide is placed under an atmosphere of nitrogen, chilled to 10°C. and carbonyldiimidazole (3.2 g, 0.02 mole) is added in one portion. After the mixture has warmed to room temperature the flask is evacuated for 15 minutes to remove the carbon dioxide evolved in formation of the imidazolide. The solution is chilled to 10°C. and a solution of 6-aminopenicillanic acid (4.4 grams, 0.02 mole) and triethylamine (5 grams, 20% excess) in chloroform (50 ml) is added. The reaction mixture is stirred at 10°C. for 1 hour, warmed to room temperature and stirring is continued for an additional 3 hours.

Ten ml of a 2 N solution of sodium 2-ethylhexanoate is added and precipitation of the product is completed by the addition of ether (700 ml). The product is filtered, reprecipitated from methanol with ether and vacuum dried to give 6.2 grams of a white solid, m.p. 180°C. (dec.) iodine titration indicates 86.6% purity.

By substituting a silylated 7-aminocephalosporanic acid, 7-aminodesacetylcephalosporanic acid, 7-amino-3-[(5-methyl-1,3,4-thiadiazol-2-ylthio)methyl]decephalosporanic acid and 7-amino-3-[(1-methyl-1,2,3,4-tetrazol-5-ylthio)methyl]decephalosporanic acid for the triethylammonium 6-aminopenicillanic acid and following essentially the same procedure one obtains the sodium salts of 7-[2-(3-methoxy-2-oxo-1-pyridinyl)acetylamino]cephalosporanic acid, 7-[2-(3-methoxy-2-oxo-1-pyridinyl)acetylamino]desacetylcephalosporanic acid, 7-[2-(3-methoxy-2-oxo-1-pyridinyl)acetylamino]-3-[(5-methyl-1,3,4-thiadiazol-2-ylthio)-methyl]decephalosporanic acid and 7-[2-(3-methoxy-2-oxo-1-pyridinyl)acetylamino]-3-[(1-methyl-1,2,3,4-tetrazol-5-ylthio)methyl]decephalosporanic acid.

EXAMPLE 7

6-[2-(5-Amino-2-oxo-1-pyridinyl)acetylamino]penicillanic acid, sodium salt

Two grams of a 10% palladium catalyst on carbon is added to a solution of 3 grams (0.0066 mole) of 3,3-dimethyl-6-[2-(5-nitro-2-oxo-1(2$\underline{H}$)pyridyl)acetamido]-7-oxo-4-thia-1-azabicyclo[3.2.0]heptane-2-carboxylic acid, sodium salt in methanol (50 ml). The solution is placed under hydrogen at atmospheric pressure and stirred until the theoretical uptake (430 ml) of hydrogen is observed (40 minutes). The solution is filtered and the filtrate is diluted with ether (500 ml). The product is reprecipitated from methanol with ether and vacuum dried to give 1.9 grams of a pale pink solid, m.p. 249°C. Iodine titration indicates a 69% purity.

EXAMPLE 8

7-[2-(2-Oxo-1-pyridinyl)acetylamino]-3-[(5-methyl-1,3,4-thiadiazol-2-ylthio)methyl]decephalosporanic acid, sodium salt A solution of 2-pyridone-1-acetic acid (2.06 grams, 0.013 mole) in dimethylformamide (40 ml) is chilled to 10°C., placed under an atmosphere of nitrogen and carbonyldiimidazole (2.18 grams, 0.013 mole) is added in one portion. The reaction mixture is stirred at room temperature for 1 hour and evacuated for 30 minutes. The mixture is chilled to −30°C. and a solution of silylated 7-amino-3-[(5-methyl-1,3,4-thiadiazol-2-ylthio)-methyl]decephalosporanic acid [from 4.6 grams (0.013 mole) of the amine and 8 ml of hexamethyldisilazane] in chloroform (40 ml) is added.

The reaction mixture is stirred cold at −20°C. for 2 hours, warmed to room temperature and stirred for an additional 18 hours. Methanol (2 ml) is added, the mixture is stirred for 30 minutes and filtered. The filtrate is decolorized and 10 ml of a sodium 2-ethylxanoate solution (2 N) in n-butanol is added. The product is precipitated with ether (700 ml) and vacuum dried to give a tan solid, m.p. 193°C.

Following essentially the same procedure but substituting 7-amino-3-[(1-methyl-1,2,3,4-tetrazol-5-ylthio)-methyl]decephalosporanic acid for the 7-amino-3-[(5-methyl-1,3,4-thiadiazol-2-ylthio)methyl]decephalosporanic acid above, results in the formation of 7-[2-(2-oxo-1-pyridinyl)acetylamino]-3-[(1-methyl-1,2,3,4- tetrazol-2-ylthio)methyl]decephalosporanic acid, sodium salt.

EXAMPLE 9

7-[2-(2-Oxo-1-pyridinyl)acetylamino]-3-(pyridiniummethyl)decephalosporanic acid

7-[2-(2-Oxo-1-pyridinyl)acetylamino]cephalosporanic acid, sodium salt is dissolved in water and reacted with pyridine in the presence of potassium thiocyanate at 60° for 6 hours. Work-up is conducted according to J. L. Spencer, et al., J. Org. Chem. 32, 500 (1967) and yields 7-[2-(2-oxo-1-pyridinyl)acetylamino]-3-(pyridiniummethyl)decephalosporanic acid as the Zwitterion.

EXAMPLE 10

7-[2-(2-Oxo-1-pyridinyl)acetylamino]desacetylcephalosporanic acid

7-[2-(2-Oxo-1-pyridinyl)acetylamino]cephalosporanic acid, sodium salt, is treated with an acetyl esterase isolated from orange peel according to J. D'A. Jeffery, et al., Biochem. J. 81, 591 (1961) to yield 7-[2-(2-oxo-1-pyridinyl)acetylamino]desacetylcephalosporanic acid, sodium salt.

EXAMPLE 11

Specific nutrient agar plates are completely innoculated with the various test organisms. Filter paper discs are placed on the surface of the agar and wetted with 0.1 ml of a solution containing 10, 100 and 1,000 micrograms of the test compound. Zones of inhibition of microbial growth are used to indicate the antibacterial activity of the test compound against the various test organisms employed.

The following table summarizes the in vitro activity in terms of a concentration required to inhibit the growth of various typical bacteria for the following representative compounds: 6-[2-(2-oxo-1-pyridinyl)acetylamino]penicillanic acid, sodium salt (1), 7-[2-(2-oxo-1-pyridinyl)acetylamino]desacetoxycephalosporanic acid, sodium salt (2), 6-[2-(6-methyl-2-oxo-1-pyridinyl)acetylamino]pencillanic acid (3), 6-[2-(2-oxo-1-pyridinyl)-2-methylacetylamino]penicillanic acid (4), 6-[2-(5-chloro-2-oxo-1-pyridinyl)acetylamino]penicillanic acid (5), 6-[2-(5-nitro-2-oxo-1-pyridinyl)acetylamino]penicillanic acid (6), 6-[2-(5-amino-2-oxo-1-pyridinyl)acetylamino]penicillanic acid (7), 6-[2-(3-methoxy-2-oxo-1-pyridinyl)acetylamino]penicillanic acid (8), and 7-[2-(2-oxo-1-pyridinyl)acetylamino]cephalosporanic acid (9).

What is claimed is:
1. A compound having the formula:

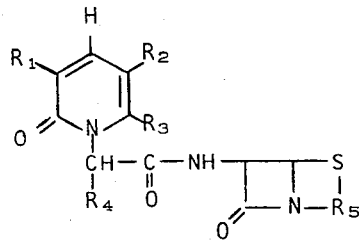

in which either $R_1$ or $R_2$ is selected from the group consisting of hydrogen, halogen, hydroxyl, lower alkyl, trifluoromethyl, nitro, amino, cyano, carboxy, carbomethoxy and carbethoxy;

$R_3$ is selected from the group consisting of hydrogen, halogen, hydroxyl, lower alkyl, trifluoromethyl, nitro, amino, cyano, carboxy, carbomethoxy, carbethoxy, and which when taken in combination with $R_2$ forms the cyclic radical $-CH_2CH_2CH_2CH_2-$ and $-CH=CH-CH=CH-$;

$R_4$ is selected from the group consisting of hydrogen, methyl, carboxy, carbomethoxy and carbethoxy;

$R_5$ is

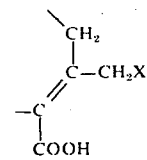

wherein X is hydrogen, hydroxy, acetoxy, N-pyridinium 5-methyl-1,3,4-thiadiazol-2-ylthio and 1-methyl-1,2,3,4-tetrazol-5-ylthio; and the pharmaceutically acceptable salts thereof.

2. A 7-[substituted (2-oxo-1-pyridinyl)acetylamino]-cephalosporin derivative according to claim 1 wherein $R_5$ is the radical

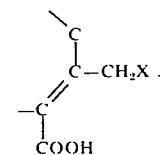

3. A compound according to claim 2 wherein X is acetoxy.

| Compound | MINIMAL INHIBITING CONCENTRATION (mcg/ml) | | | | |
|---|---|---|---|---|---|
| | Staphylococcus aureus | Salmonella schottmuelleri | Streptococcus pyogenes | (Penicillinase Producing) Staphylococcus aureus | Acid Resistance |
| (1) | 10 | 1,000 | 10 | 1,000 | Yes |
| (2) | 1,000 | >1,000 | 1,000 | >1,000 | Yes |
| (3) | 10 | 1,000 | 1,000 | 1,000 | Yes |
| (4) | 1,000 | 1,000 | 1,000 | 1,000 | Weak |
| (5) | 10 | 1,000 | 1,000 | >1,000 | Yes |
| (6) | 10 | 1,000 | >1,000 | >1,000 | Yes |
| (7) | 10 | 1,000 | >1,000 | >1,000 | Yes |
| (8) | 10 | 1,000 | — | 1,000 | Yes |
| (9) | 10 | 100 | 10 | 1,000 | Yes |

4. A compound according to claim 1 wherein $R_4$ is hydrogen.

5. A compound of claim 1 which is 7-[2-(2-oxo-1-pyridinyl)acetylamino]cephalosporanic acid and the pharmaceutically acceptable salts thereof.

* * * * *